United States Patent [19]

Tencza et al.

[11] Patent Number: 4,943,565

[45] Date of Patent: Jul. 24, 1990

[54] ANALGESIC TABLET OF ASPIRIN AND CAFFEINE CONTAINING LOW-SUBSTITUTED HYDROXYPROPYL CELLULOSE

[75] Inventors: Thomas M. Tencza, Wallington; Chung-Bin Kim, Livingston, both of N.J.

[73] Assignee: Bristol-Myers Squibb Company, New York, N.Y.

[21] Appl. No.: 282,983

[22] Filed: Dec. 2, 1988

Related U.S. Application Data

[63] Continuation of Ser. No. 132,717, Dec. 11, 1987, abandoned, which is a continuation of Ser. No. 907,697, Sep. 15, 1986, abandoned.

[51] Int. Cl.$^5$ ............... A61K 31/16; A61K 31/52; A61K 31/62
[52] U.S. Cl. ............... 514/161; 514/263; 514/629
[58] Field of Search ............... 514/161, 263, 629

[56] References Cited

PUBLICATIONS

Chem. Abst., vol. 89, 1978-117706p.
Y. Machida et al., Directly Compressed Tablets Containing Hydroxypropylcellulose in Addition to Starch or Lactose, Chem. Pharm. Bull., 22:2346-51 (1974).
Y. Machida et al., Application of Hydroxypropylcellulose to Peroral Controlled Release Dosage Forms, Chem. Pharm. Bull., 26:1652-58 (1978).
L-HPC, Low-Substituted Hydroxypropylcellulose Tech. Bull., Shin-Etsu Chemical Company.
Pharm. Tech. Japan, V. 5, No. 5, Advertisement, "Application of Nisso HPC" (1989).
Pharm. Tech. Japan, vol. 5, No. 5, Advertisement, "Application for Matrix Preparation" (1989).
Pharmacopoeia of Japan, pp. 1247-1251 (11th Edition, 1986).
C. Caramella et al., The Role of Swelling in the Disintegration Process, Int. J. Pharm. Tech & Prod. Mfr., 5: 1-5 (1984).

*Primary Examiner*—Stanley J. Friedman
*Attorney, Agent, or Firm*—Charles J. Zeller

[57] ABSTRACT

An analogesic tablet containing aspirin, acetaminophen and caffeine of improved dissolution rate containing low-substituted hydroxypropylcellulose.

10 Claims, No Drawings

ANALGESIC TABLET OF ASPIRIN AND CAFFEINE CONTAINING LOW-SUBSTITUTED HYDROXYPROPYL CELLULOSE

This application is a continuation of application Ser. No. 132,717, filed Dec. 11, 1987, which is a continuation of application Ser. No. 907,697, filed Sept. 15, 1986, both now abandoned.

This invention relates to tablets containing, in combination, aspirin, acetaminophen and caffeine. More particularly it concerns tablets of this character having improved dissolution rates.

The combination of aspirin, acetaminophen and caffeine is popular in analgesic preparations and finds widespread use, particularly in over-the-counter (O.T.C) products. Moreover, a widely used dosage form for delivering this combination drug is still the tablet. Since these products are also likely to be subjected to elevated temperatures while in storage in warehouses and in homes, it has become customary in course of manufacturing such tablets to store them at elevated temperatures for extended periods of time to test their stability and the in-vitro availability of the active ingredients; i.e., aspirin, acetaminophen and caffeine for pharmaceutical action. One method for measuring the latter has been to measure the dissolution rates of the tablets. If the tablets meet a certain standard for dissolution rate, the active ingredients should be available for absorption into the blood stream within an acceptable period of time after ingestion.

Aspirin, acetaminophen, or caffeine when use separately in tablets or the combination of aspirin and acetaminophen in tablets have not presented any particular problem with respect to the acceptability of their dissolution rates. However, when all three are combined in a tablet, serious problems do arise. Such tablets have proven to have dissolution rates which do not meet the standards set. The reason for this is not clearly understood. Nevertheless, it is known that the three ingredients react physically to form a eutectic mixture. This is manifested by a slowdown in the dissolution rate of aspirin accompanied by a high free salycilic acid (FSA) level resulting from the hydrolysis of the aspirin.

It is now been found, quite unexpectedly, that the dissolution rates of tablets containing aspirin, acetaminophen and caffeine that have been stability tested under various conditions can be dramatically improved by incorporating in said tablet a low-substituted hydroxypropylcellulose (hereinafter referred to as L-HPC) in sufficient amount to serve as a secondary disintergrant.

C. Caramella, et al, in their article, "The Roll of Swelling in the Disintegration Process", Int. J. Pharm. Tech. & Prod. Mfr. 5(2) 1–5, 1984, studied the disintegrating process of certain specific tablets and the relationship of the character of certain disintegrants to the disintegration process. The tablets employed in these studies were a series of tablets containing 500 mg of aspirin, 2% talc and 4% disintegrant. Among the several disintegrants tested, the authors mention L-HPC and Polyplasdone XL. The authors conclude that disintegration efficiency is related to what is referred to as the swelling force and particularly the "disintegrating force development rate". In Table 3 of this article at the top of page 4 the authors summarize certain of their results. Thus they note that the disintegrating force developed in the tablet containing Polyplasdone XL is 4.3±0.1 in both isotonic saline and 0.1N HCl, but for L-HPC the values were 2.2±0.1 and 2.0±0.2.Similarly, for the disintegration time in the tablet containing Polyplasdone XL, the value was 10±0.2 and 9±0.2 sec.; whereas, for the aspirin tablet containing L-HPC, the values were 18±3 and 19±3 sec. On the basis of this study, one skilled in the art might expect that if L-HPC were incorporated in a tablet containing aspirin, acetaminophen and caffeine that the dissolution rate would be lower than that obtained with the use of Polyplasdone XL. As will be shown in more detail below, unexpectedly, the reverse has been found to be the case and the dissolution rates were higher with the use of L-HPC than with the Polyplasdone XL. This dissolution rate was measured as the time in minutes that it takes to dissolve 75% of the active ingredients in the tablet. Accordingly, the lower the value, the greater the dissolution rate.

In their search for a suitable disintegrant that would give the desired results, applicants have tested a number of materials all of which proved to be unsatisfactory. Thus, other cellulose material such as Ac-Di-Sol (internally cross-linked form of sodium carboxymethylcellulose) was tried without success. It produced only a marginal benefit in dissolution rate while affecting the stability of the aspirin negatively generating high values of FSA. Similarly such commercially available disintegrants as Explotab and Primogel were tried and also found unacceptable.

The L-HPC's that are useful for the practice present are available in a variety of grades that are classified on the basis of their % hydroxypropyl content. These extend over the range of from about 10% to about 16% hydroxypropyl. Of special utility in the present invention are the L-HPC's that contain a hydroxypropyl content of from about 10% to about 13%. Such products are sold on the market by the Shin-Etsu Chemical Company under the trade designation low-substituted hydroxypropylcellulose Grade LH-21 or LH-11. These differ from each other in particle size.

These materials conform to the general formula,

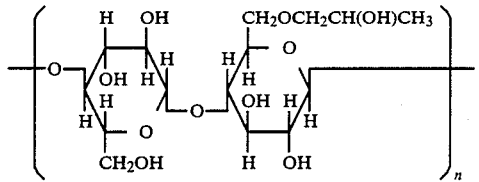

wherein n is the degree of polymerization. They are non-ionic type cellulose ethers with a neutral pH range (5.0–7.5) that do not react with amines or other ionic ingredients. The particle size of these materials may vary somewhat. However, in the preferred grade (LH-21) the particle sizes are as follow:

74 um pass: not less than 90%
105 um on: less than 1%

The quantity of L-HPC that will be contained in the tablets of the present invention may vary somewhat. However, again quite unexpectedly, it has been found as little as 1% or less of the L-HPC, based on the total weight of the tablets, have given excellent results. This is to be contrasted with the concentrations of from 3%–15% which have been recommended for these materials when used as a binder/disintegrant for tablets. Generally, in accordance with this invention, the L-HPC will constitute from about 0.5% to about 5% by weight based on the total weight of the tablet. However, the preferred range for the L-HPC is from about 0.8% to about 2.0% on the same weight basis.

The aspirin, acetaminophen and caffeine will be contained in the present tablets at concentrations at which these ingredients are generally employed in analgesic tablets. That is to say that they will be contained in analgesic quantities. However, the general ranges and the preferred ranges for these ingredients are those that are given in the table below expressed in terms of percent by weight based on the total weight of the tablet.

TABLE I

| Ingredient | % W/W of Tablet | |
|---|---|---|
| | General Range | Preferred Range |
| Aspirin | from about 22% to about 75% | from about 30% to about 45% |
| Acetaminophen | from about 22% to about 75% | from about 30% to about 45% |
| Caffeine | from about 4% to about 19% | from about 9% to about 11% |

The products of the present invention will be made up into tablets that may be taken comfortably by oral administration. Again, the quantity of ingredients that will be contained in each tablet may vary over a range. Table II below gives the general and preferred quantity range of the ingredients contained in each tablet expressed in terms of mg/tablet.

TABLE II

| Ingredient | mg/Tablet | |
|---|---|---|
| | General Range | Preferred Range |
| L-HPC | about 5 mg to about 35 mg | about 5 mg to about 10 mg |
| Aspirin | about 150 mg to about 500 mg | about 200 mg to about 300 mg |
| Acetaminophen | about 150 mg to about 500 mg | about 200 mg to about 300 mg |
| Caffeine | about 30 mg to about 130 mg | about 60 mg to about 70 mg |

In addition to the L-HPC, aspirin, acetaminophen and caffeine, the tablets of the present invention may also contain other tablet adjuvants that are well known to those skilled in this art. These are added for a number of purposes, e.g. facilitate tableting, improve the organoleptics of the tablet, improve stability of the tablet, improve the ease of administration of the tablets, etc. By way of example, tablet adjuvants that may be incorporated in the present tablet include lubricants (e.g. stearic acid, zinc stearate), flow agents (e.g. fumed silica, precipitated silica), and wetting agents (Tween 80, sodium lauryl sulfate).

No special technique is required to prepare the tablets of this invention. Generally, the ingredients will be dry blended (e.g. Twin Shell Blender) and the mixture is then filled into a tablet press and then compressed into a tablet. Alternatively, the L-HPC can be incorporated into wet granulations of the other ingredients and the mixture then compressed into tablets.

The regimen for administering the tablets of this invention may vary somewhat depending on the size of the tablets, the recommended daily dose for the ingredient, and the condition being treated with these tablets. Generally, this will amount to about 1 to 2 tablets with each dose about 4 times a day and preferably 1 to 2 tablets 3 or 4 times a day.

The following examples are given to further illustrate the present invention. It is to be understood, however, that the invention is not limited thereto.

EXAMPLE 1

Formula CW 3446-58

| Dosage Unit Amt mg/Tablet | Item No. | Ingredients | % W/W |
|---|---|---|---|
| 75.00 | 1 | Aspirin 40 mesh | 11.12760 |
| 175.00 | 2 | Aspirin 80 mesh | 25.96439 |
| 250.00 | 3 | Acetaminophen Granular | 37.09199 |
| 65.00 | 4 | Caffeine, Anhydrous Powder | 9.64392 |
| 100.00 | 5 | Cellulose, Microcrystalline | 14.83679 |
| 5.00 | 6 | Low-substituted Hydroxypropyl Cellulose Grade LH-21 (Shin-Etsu Chemical Co.) | 0.74184 |
| 4.00 | 7 | Stearic Acid, Powdered | 0.59347 |
| 674.00 | | | 100.00000 |

Procedure:
A. Screen caffeine through a #20 mesh screen.
B. Screen stearic acid through a #50 mesh screen.
C. Mix all ingredients except stearic acid for 15 minutes in a Twin Shell Blender.
D. Add stearic acid to (C) and mix for five minutes.
E. Compress to specifications shown below.
Appearance: White Tablets
Punch: 7/16"
Tablet Weight: 674.0 mg.
Thickness: 0.245" ± 0.005"
Hardness: 15-20 SCU (Heberlein)
Disintegration: water, 37° C./1 min.
USP basket apparatus

EXAMPLE 2

Formula CW 3446-38 B

| Dosage Unit Amt mg/Tablet | Item No. | Ingredients |
|---|---|---|
| 75.00 | 1 | Aspirin 40 mesh |
| 175.00 | 2 | Aspirin 80 mesh |
| 250.00 | 3 | Acetaminophen Granular U.S.P. Mallinckrodt, Grade 0057 |
| 65.00 | 4 | Caffeine, Anhydrous Powder |
| 100.00 | 5 | Cellulose, Microcrystalline |
| 2.50 | 6 | Stearic Acid |
| 5.00 | 7 | L-HPC LH-21 |
| 672.50 | | |

EXAMPE 3

Formula CW 3589-9 (8 mg L-HPC Formula)

| Dosage Unit Amt mg/Tablet | Item No. | Ingredients |
|---|---|---|
| 75.00 | 1 | Aspirin 40 mesh |
| 175.00 | 2 | Aspirin 80 mesh |
| 250.00 | 3 | Acetaminophen Granular U.S.P. |
| 65.00 | 4 | Caffeine, Anhydrous Powder |
| 100.00 | 5 | Cellulose, Microcrystalline |
| 2.50 | 6 | Stearic Acid |
| 8.00 | 7 | L-HPC LH-21 |
| 675.50 | | |

EXAMPLE 4

| Formula CW 3446-94 (10 mg L-HPC Formula) | | |
| --- | --- | --- |
| Dosage Unit Amt mg/Tablet | Item No. | Ingredients |
| 75.00 | 1 | Aspirin 40 mesh |
| 175.00 | 2 | Aspirin 80 mesh |
| 250.00 | 3 | Acetaminophen Granular U.S.P. |
| 65.00 | 4 | Caffeine, Anhydrous Powder |
| 100.00 | 5 | Cellulose, Microcrystalline |
| 2.50 | 6 | Stearic Acid |
| 10.00 | 7 | L-HPC LH-21 |
| 677.50 | | |

The procedure for Examples 2, 3 and 4 are similar to that described in Example 1.

Two criteria are important in determining the acceptability of tablets containing aspirin, acetaminophen and caffeine. One is the dissolution rate of the tablet after storage for a period of time and the second is the FSA (free salicylic acid) analysis. The first is important in that it is an in-vitro indication of the availability of the active ingredients for absorption into the blood stream. The second is important since it is a measure of the stability of the tablet. High FSA values indicate that significant aspirin hydrolysis has taken place with the release of free salicylic acid.

Tests were carried out comparing the dissolution rates and/or the FSA values of tablets of the present invention with essentially two different types of tablets. The first category of tablets are essentially the same as those of the present invention excepting that they do not contain the L-HPC. The second category of tablet are those in which a different disintegrating agent is employed.

The tablets of this invention were tested after storage at various conditions of time and temperature and in various types of containers and found to give acceptable dissolution rates and FSA values. To insure that the tablets would perform acceptably under all the reasonably anticipated field conditions' in their tests applicants also stored the tablets under stressed conditions and measured their performance after such treatment. These stress conditions are described in more detail below. For purposes of comparison other tablets were also subjected to these stress conditions and their dissolution rate and FSA values were determined.

Test Procedure

A. Stress Testing:

Test Tablets stored at room temperature in glass bottles; this was the unstressed storage condition. Other samples of the same tablet were stored at 60° C. and 60% relative humidity in an open petri dish for 6 days. The latter are considered stress conditions. FSA values were determined on test tablets that were stress tested; i.e., stored at 60° C. and 60% relative humidity in an open petri dish for 6 days.

B. Dissolution Rate Test:

The dissolution method used to evaluate these tablets employs the dissolution test described in the USPXXI p. 14. The dissolution test calls for the use of 900 ml. water maintained at 37° C. and the USP paddle, known as apparatus 2, rotated at 50 rpm.

The tablet is placed in the beaker of water and after 45 minutes of paddle rotation at 50 rpm, an aliquot of solution is analyzed for aspirin, acetaminophen and caffeine content.

The analysis can be done via high pressure chromatography or via spectrophotometric analysis using a multi-component analysis on HP8450 or HP8451 spectrophotometer.

As a criteria for acceptability, applicants have adapted a dissolution rate such that at least 75% of the tablet dissolves in under 45 minutes.

Table III below gives the formulas for each of the tablets which were tested. The quantities of the various ingredients are given in terms of mg/tablet.

TABLE III

| Ingredient | *CW-3446-38B | *CW-3446-38A | *CW-3446-54B | *CW-3446-58 | CY3513-1 |
| --- | --- | --- | --- | --- | --- |
| Aspirin, 40 mesh | 75 | 75 | 75 | 75 | — |
| Aspirin, 80 mesh | 175 | 175 | 175 | 175 | — |
| Acetaminophen | 250 | 250 | 250 | 250 | — |
| Caffeine, Anhy. Powder | 65 | 65 | 65 | 65 | — |
| Microcrystalline Cellulose | 100 | 100 | 100 | 100 | — |
| Stearic Acid | 2.5 | 2.5 | 2.5 | 4 | 3 |
| L-HPC #LH21 | 5 | — | — | 5 | — |
| Crospovidone XL-10 (Polyplasdone XL-10) | — | — | 5 | — | — |
| Caffeine Starch Granulation (Eq. to 65 mg. Caffeine) | — | — | — | — | 100 |
| Aspirin 12/50 Granulation (Eq. to 250 mg. Aspirin) | — | — | — | — | 277.8 |
| APAP 10% Starch 145 (Eq. to 250 mg APAP) | — | — | — | — | 277.8 |
| TOTAL | 672.5 | 667.50 | 672.5 | 674.0 | 658.6 |

*Subjected to stress test.

The results of these tests are summarized in Table IV below. It will be noted that the tablets CW 3446-38A do not meet the criteria of a dissolution of 75% of the tablet in under 45 minutes, whereas, tablets CW 3446-38B do so readily. As is clear from Table III, tablets CW-3446-

38A differ from CW-3446-38B in that the latter also contain 5mg of L-HPC #LH21. Similarly it is to be former is 2.2 mg/tab, whereas, in the latter it is 0.57 mg/tab. This is about 4 times as much.

TABLE IV

Dissolution Rates
1/900 ml H₂O/37°/Paddle 50 rpm

Time (minutes)

| Tablet | T25 | | | T50 | | | T75 | | | T80 | | |
|---|---|---|---|---|---|---|---|---|---|---|---|---|
| | ASA | APAP | CAFF | ASA | APAP | CAFF | ASA | APAP | CAFF | ASA | APAP | CAFF |
| CW3446-38A | | | | | | | | | | | | |
| RT | 23 | 7 | 4 | 28 | 15 | 8 | 44 | 27 | 14 | 45 | 29 | 18 |
| 60° C./60% RH 6 days | 20 | 15 | 9 | 45 | 29 | 18 | 45 | 45 | 31 | 45 | 45 | 36 |
| CW3446-38B | | | | | | | | | | | | |
| RT | 3 | 2 | 1 | 5 | 4 | 3 | 19 | 7 | 8 | 13 | 8 | 7 |
| 60° C./60% RH 6 days | 8 | 4 | 3 | 9 | 7 | 8 | 16 | 11 | 11 | 18 | 13 | 12 |
| CW-3446-54B | | | | | | | | | | | | |
| RT | 2 | 2 | 1 | 4 | 3 | 2 | 9 | 6 | 4 | 10 | 6 | 5 |
| 60° C./60% RH 6 days | 27 | 11 | 8 | 45 | 27 | 16 | 45 | 45 | 27 | 45 | 45 | 30 |
| | | | | (2 tab) | | | (2 tab) | (2 tab) | | | | |

Stability: 60° C./60% R.H. in open petri dish 6 days.

| | Salicylic Acid mg/tab |
|---|---|
| CW 3446-38A | 0.46 |
| CW 3446-38B | 0.57 |
| CW 3446-54B | 2.2 | noted that tablets CW 3446-54B also do not meet the criteria of a dissolution of 75% of the tablet in under 45 minutes. Tablets CW 3446-54B, as Table 111 shows, contain 5mg of Polyplasdone XL-10 as a disintegrant, whereas, tablets CW 3446-38B of this invention contain 5mg of L-HPC #1H21 as the disintegrant. In addition, the product containing the Polyplasdone XL-10 (CW 3446-54B) is less stable after stress testing than the product of this invention (CW 3446-38B). The amount of salicylic acid produced by degeneration of aspirin in the Tablets CW 3446-58 involved in this invention were also compared to a comparable product that does not contain the L-HPC. LH21 disintegrant; i.e., tablets CY 3513-1 (see Table III), as to their dissolution rate at various conditions of storage and in different types of containers. In addition, they were also compared as to their stability as measured by the FSA values. These measurements were made after 2 months storage. The results of these studies are summarized in Table V below.

TABLE V

Dissolution Rates
1/900 ml H₂O/37° C./Paddle 50 rpm

Time (minutes)

| Tablet | T25 | | | T50 | | | T75 | | |
|---|---|---|---|---|---|---|---|---|---|
| | ASA | APAP | CAFF | ASA | APAP | CAFF | ASA | APAP | CAFF |
| CW 3446-58 | | | | | | | | | |
| Initial Two Months Polystyrene/ Safety Cap | 2 | 2 | 1 | 4 | 3 | 2 | 7 | 5 | 4 |
| RT | 3 | 2 | 1 | 5 | 4 | 3 | 9 | 7 | 6 |
| 125/F | 5 | 2 | 2 | 11 | 5 | 4 | 26 | 12 | 11 |
| H/H Polyethylene/ Safety Cap | 12 | 8 | 7 | 20 | 15 | 12 | 32 | 24 | 20 |
| 125/F | 11 | 7 | 6 | 18 | 12 | 10 | 26 | 20 | 16 |
| H/H Slide Box | 4 | 3 | 2 | 8 | 6 | 5 | 13 | 10 | 9 |
| H/H | 10 | 7 | 6 | 16 | 12 | 10 | 24 | 19 | 18 |
| CY 3513-1 | | | | | | | | | |
| Initial Two Months Polystyrene/ Safety Cap | 3 | 2 | 2 | 6 | 4 | 3 | 14 | 6 | 6 |
| RT | 3 | 3 | 3 | 7 | 5 | 5 | 14 | 10 | 9 |
| 125/F | 3 | 2 | 2 | 6 | 4 | 3 | 12 | 7 | 7 |
| H/H Polyethylene/ Safety Cap | 19 | 6 | 8 | 36 | 15 | 17 | 45 (3) | 30 | 31 |
| 125/F | 23 | 7 | 10 | 41 | 17 | 24 | 45 (4) | 36 | 45 (1) |
| H/H Slide Box | 8 | 5 | 5 | 14 | 8 | 9 | 27 | 12 | 12 |
| H/H | 7 | 3 | 4 | 13 | 6 | 7 | 25 | 10 | 11 |

TABLE V-continued

| Stability: | Salicylic Acid, Mg/Tab., 1 Month 104° F./75% RH | | | |
|---|---|---|---|---|
| | 125/F P/S S. Cap | HD/PE S. Cap | P/S Slide Box | HD/PE S. Cap |
| CW 3446-58 | 1.7 | 0.7 | 2.2 | 3.0 |
| CY 3513-1 | 0.6 | 0.5 | 1.1 | 3.4 |

As is clear from Table V, tablets CY 3513-1 are acceptable only when packaged in a slide box. Tablets CW 3446-58, however, were acceptable under all the storage conditions; that is to say, they had an acceptable dissolution rate. As to stability, these respective products are quite comparable.

What is claimed is:

1. In a tablet containing by weight of the tablet about 22-75% aspirin, about 22-75% acetaminophen and about 4-19% caffeine, said tablet dissolving in a predetermined period of time, the improvement comprising incorporating into said tablet a dissolution enhancing amount of a hydroxypropyl cellulose ether nonionic polymer which has a hydroxypropyl content of from about 10% to about 16% by weight of the polymer, whereby said polymer-containing tablet dissolves in less than said predetermined period of time.

2. The tablet according to claim 1, wherein the hydroxypropyl cellulose is incorporated in the tablet in an amount of from about 0.5% to about 5% by weight, based on the total weight of the tablet.

3. The tablet according to claim 1, wherein the hydroxypropyl cellulose is present in the tablet in an amount of from about 0.8% to about 2.0% by weight, based on the total weight of the tablet.

4. The tablet according to claim 1, wherein the hydroxypropyl content is from about 10% to about 13%.

5. The tablet according to claim 1 wherein the tablet contains, based on the total weight of the tablet, from about 0.5% to about 5% by weight hydroxypropyl cellulose.

6. The tablet according to claim 5, wherein the aspirin is present in an amount of from about 30% to about 45% by weight, the acetaminophen is present in an amount of from about 30% to about 45% by weight, and the caffeine is present in an amount of from about 9% to about 11% by weight.

7. The tablet according to claim 1, wherein the tablet contains from about 150 mg. to about 500 mg. aspirin, from about 150 mg. to about 500 mg. acetaminophen, from about 30 mg. to about 130 mg. caffeine and from about 5 mg. to about 35 mg. of the hydroxypropyl cellulose.

8. The tablet according to claim 1, wherein the tablet contains from about 200 mg. to about 300 mg. aspirin, from about 200 mg. to about 300 mg. acetaminophen, from about 60 mg. to about 70 mg. caffeine and from about 5 mg. to about 10 mg. hydroxypropyl cellulose.

9. In a tablet containing by weight of the tablet about 22-75% aspirin, about 22-75% acetaminophen and about 4-19% caffeine, said tablet dissolving in a predetermined period of time, the improvement comprising incorporating into said tablet, based on the total weight of the tablet, from about 0.5 to about 5% by weight of a cellulose ether nonionic polymer which has a hydroxypropyl content of from about 10% to about 16% by weight of the polymer, whereby said polymer-containing tablet dissolves in less than said predetermined period of time.

10. The tablet according to claim 9, wherein the hydroxypropyl content is from about 10% to about 13%.

* * * * *